United States Patent [19]

Gervasutti et al.

[11] Patent Number: 5,118,888
[45] Date of Patent: Jun. 2, 1992

[54] PROCESS FOR THE PREPARATION OF 1,2-DIFLUORO-ETHYLENE AND 1-CHLORO-1,2-DIFLUORO-ETHYLENE

[75] Inventors: Claudio Gervasutti, Mestre; Giorgio Guglielmo, Mirano; Luigi Marangoni, Fiesso D'Artico, all of Italy

[73] Assignee: Ausimont S.p.A., Milan, Italy

[21] Appl. No.: 528,896

[22] Filed: May 29, 1990

Related U.S. Application Data

[63] Continuation of Ser. No. 244,566, Sep. 12, 1988, abandoned, which is a continuation of Ser. No. 871,826, Jun. 9, 1986, abandoned.

[30] Foreign Application Priority Data

Jun. 10, 1985 [IT] Italy .................... 21088 A/85

[51] Int. Cl.⁵ .................... C07C 17/24; C07C 21/18
[52] U.S. Cl. .................... 570/153
[58] Field of Search .................... 570/153

[56] References Cited

U.S. PATENT DOCUMENTS

| 2,704,775 | 3/1955 | Clark | 570/156 |
| 2,802,887 | 8/1957 | Miller et al. | 570/156 |
| 3,564,064 | 2/1971 | Nakagawa | 570/156 |

FOREIGN PATENT DOCUMENTS 542435  6/1957  Canada .................... 570/156

Primary Examiner—J. E. Evans
Attorney, Agent, or Firm—Morgan & Finnegan

[57] ABSTRACT

Process for the preparation of 1,2-difluoro-ethylene and 1-chloro-1,2-difluoroethylene by catalytic hydrogenation of 1,2-dichloro-difluoro-ethylene.

5 Claims, No Drawings

PROCESS FOR THE PREPARATION OF 1,2-DIFLUORO-ETHYLENE AND 1-CHLORO-1,2-DIFLUORO-ETHYLENE

This application is a continuation of application Ser. No. 244,566, filed Sep. 12, 1988 which is a continuation of Ser. No. 871,826, filed Jun. 9, 1986, both now abandoned.

BACKGROUND OF THE INVENTION

1. Field of the Invention

The present invention relates to a process for the preparation of 1,2-difluoro-ethylene and of 1-chloro-1,2-difluoro-ethylene.

In particular, the present invention relates to a process for the preparation of 1,2-difluoro-ethylene and of 1-chloro-1,2-difluoro-ethylene by starting from 1,2-dichloro-difluoro-ethylene.

2. Description of the Prior Art 1,2-Difluoro-ethylene and 1-chloro-1,2-difluoro-ethylene are haloolefins well known in the technical literature, and are valuable materials for use as intermediates in the preparation of fluoroplastomers, fluoroelastomers, rubber stabilizers and as monomers in the preparation of fluorinated copolymers.

1-Chloro-1,2-difluoro-ethylene is generally produced by the reduction with zinc, in alcoholic solution, of 1,2-difluoro-1,1,2-trichloro-ethane.

The high amount of zinc required by this reaction, and the difficult disposal thereof make this process not much attractive from the industrial viewpoint.

THE PRESENT INVENTION

According to the present invention, a cheap and industrially favourable process to produce 1-chloro-1,2-difluoro-ethylene, together with 1,2-difluoro-ethylene, consists in submitting to hydrogenolysis one of the carbon-chlorine bonds of 1,2-dichloro-di-fluoro-ethylene, or both of such bonds, in the presence of a hydrogenation catalyst consisting of a transition metal or of an alloy of transition metals.

Tests carried out by the Applicant have surprisingly shown that the hydrogenolysis of 1,2-dichloro-difluoro-ethylene, in the presence of one of the above said catalysts, causes the partial or total substitution of chlorine, leaving unchanged the ethylenic unsaturation of the starting compound.

1,2-Dichloro-difluoro-ethylene, used as the starting product in the process of the present invention, is a commercial product, easily obtainable by dechlorination of 1,2-difluoro-tetrachloro-ethane.

The process of catalystic hydrogenolysis of 1,2-dichloro-difluoro-ethylene can be carried out either under atmospheric or under superatmospheric pressure; pressure values of up to 15 bars can be used.

The hydrogenolysis temperature is generally higher than 100° C., and comprised within the range of from 200° C. to 600° C., preferably of from 300° C. to 400° C.

The molar ratio of hydrogen to 1,2-dichloro-difluoro-ethylene is comprised within the range of from 0.5 to 10, and preferably of from 3 to 5.

According to a preferred embodiment of the present invention, the reactants 1,2-dichloro-difluoro-ethylene and hydrogen are fed in continuous to the heated catalytic bed, and the reaction gases leaving the reactor are condensed at a temperature lower than 0° C.

In the process of the present invention, there can be used any hydrogenation catalysts consisting of a transition metal or of an alloy of transition metals, particularly Pd, Pt, Ni-Cu and Cr-Cu. Preferably, Pd is used.

The catalytic bed can be constituted by the transition metal or alloy powder either as such, or, preferably, supported on an inert material, such as charcoal, alumina, barium sulphate, and so forth, at concentrations of transition metal or alloy comprised within the range of from 0.1 to 5% by weight.

Small amounts, up to 10% by weight, of other transition metals, such as copper and chromium, can be added to palladium.

The reactants-catalyst time contact is generally comprised within the range of from 5 to 60 seconds, preferably of from 10 to 20 seconds.

Hydrogen can be fed to the reaction in its pure state, or diluted with an inert gas, such as nitrogen, helium, argon, and so forth.

The hydrogenation is generally carried out inside tubular reactors made of materials inert towards the ractants, and the reaction products and byproducts, such as nickel, Inconel, stainless steel, etc.

After leaving the reactor, the vapours of the reaction products are separated from hydrogen by washing with an aqueous alkaline solution, e.g., a solution containing 5–20% by weight of alkali metal hydroxide, they are then dried over concentrated sulphuric acid, or over $CaCl_2$ and cooled to a temperature lower than 0° C., up to complete condensation.

The process of the present invention allows a complete conversion to be obtained of 1,2-dichloro-difluoro-ethylene into the mixture of 1,2-difluoro-ethylene and 1-chloro-1,2-difluoro-ethylene, with high yields. The weight ratio between the products 1,2-difluoro-ethylene and 1-chloro-1,2-difluoro-ethylene outcoming from the reaction can range from 0.5 to 5, as a function of the reactants ratio, of the contact time and the reaction temperature. The reaction products can be separated from each other, and from the impurities by fractional distillation.

To the purpose of better understanding the present invention, the following illustrative Examples are given, which are in no way limitative of the invention itself.

In the Examples, percentages and parts are by weight, unless differently stated.

EXAMPLE 1

Into a cylindrical reactor of nickel, having an inner diameter of 2 cm and a useful volume of 160 cm$^3$, containing 100 cm$^3$ of granules of activated charcoal with a palladium content of 2% by weight, temperature-controlled at 350° C., under atmospheric pressure 0.5 mol/hour are introduced of a mixture, preheated at 105° C., of hydrogen and 1,2-dichloro-difluoro-ethylene in an $H_2/C_2Cl_2F_2$ molar ratio of 3:1.

The organic vapors leaving the reactor show, on gas-chromatographic analysis, the following composition:

1,2-difluoro-ethylene (CHF=CHF) = 53%
1-chloro-1,2-difluoro-ethylene (CHF=CCLF) = 27%
unreacted 1,2-dichloro-1,2-difluoro-1,2-difluoroethylene (CCLF=CCLF) = 4%

The balance to 100 is constituted by such byproducts as CHCLF—CHCLF, CH$_2$F—CH$_2$F and CH$_2$=CHF.

The organic reaction products are washed with a 10% NaOH solution, dried and condensed at −70° C.

EXAMPLE 2

By operating under the same conditions as of Example 1, to the same catalytic system, temperature-controlled at 300° C., a mixture is fed of hydrogen and 1,2-dichloro-difluoro-etylene with an $H_2/C_2Cl_2F_2$ molar ratio of 2:1.

The organic vapors leaving the reactor have shown, on gas-chromatographic analysis, the following percentages by weight:

1,2-difluoroethylene = 42%
1-chloro-1,2-difluoro-ethylene = 29%
1,2-dichloro-1,2-difluoroethylene = 16.4%

The balance to 100 is constituted by byproducts.

EXAMPLE 3

Into the reactor of Example 1, temperature-controlled at 300° C., a hydrogen/1,2-dichloro-difluoroethylene mixture with a molar ratio 3:1 is fed.

The organic vapors leaving the reactor have shown, on gas-chromatographic analysis, the following percentages by weight:

1,2-difluoro-ethylene = 48%
1-chloro-1,2-difluoro-ethylene = 30%
1,2-dichloro-1,2-difluoroethylene = 8.4%

The balance to 100 is constituted by byproducts.

EXAMPLE 4

Into a cylindrical reactor of nickel, temperature-controlled to 350° C., having an inner diameter of 2 cm and a useful volume of 160 cm$^3$, containing 100 cm$^3$ of granules of activated charcoal with a palladium content of 0.5% by weight, a mixture, preheated at 105° C., of hydrogen and 1,2-dichloro-difluoro-ethylene in molar ratio 2:1 is fed.

The gas-chromatographic analysis of the organic vapors leaving the reactor has given the following results:

1,2-difluoro-ethylen = 20% by weight
1-chloro-1,2-difluoro-ethylene = 25% by weight
1,2-dichloro-1,2-difluoroethylene = 40% by weight The vapors leaving the reactor are washed with an aqueous 10% NaOH, solution, dried and condensed at −70° C.

EXAMPLE 5

Into a cylindrical reactor of AISI 316, temperature-controlled at 350° C., having an inner diameter of 5.4 cm and a length of 70 cm, containing 500 cm$^3$ of granules of activated charcoal with a palladium content of 0.5% by weight, a mixture, preheated at 105° C., of hydrogen and 1,2-dichloro-difluoro-ethylene with molar ratio 3:1 is fed.

The gas-chromatographic analysis of the vapors leaving the reactor has given the following results:

1,2-difluoro-ethylene = 50% by weight
1-chloro-1,2-difluoro-ethylene = 25% by weight
1,2-dichloro-1,2-difluoroethylene = 8% by weight The balance to 100% is constituted by byproducts. The vapors are condensed at −70° C.

What is claimed is:

1. A process for the preparation of a mixture of 1,2-difluoroethylene and 1-chloro-1,2-difluoroethylene from 1,2-dichloro-difluoroethylene comprising reacting 1,2-dichloro-difluoroethylene with $H_2$ at a temperature between 300° and 400° C. in the presence of a hydrogenation catalyst comprising Pd or an alloy thereof, the hydrogen/1,2-dichloro-difluoroethylene molar ratio being between 3 and 5, while the contact time of the reactants with the catalyst is between 10 and 20 seconds whereby a weight ratio between 1,2-difluoroethylene and 1-chloro-1,2-difluoroethylene ranging from 0.5 to 5 can be obtained.

2. A process according to claim 1 wherein 1,2-dichloro-difluoroethylene is reacted with $H_2$ at a temperature between 350° and 400° C.

3. A process according to claim 1, wherein the reaction is carried out at a pressure between atmospheric pressure and 15 bars.

4. A process according to claim 1, wherein the hydrogenation catalyst is supported on an inert material at a concentration within the range of from 0.1 to 5% by weight.

5. A process according to claim 1, wherein the reactants 1,2-dichloro-difluoro-ethylene and hydrogen are continuously fed to a heated catalytic bed, and the reaction vapors leaving the reactor are condensed at a temperature lower than 0° C., after being preliminarily washed with an aqueous alkaline solution and dried.

* * * * *